US00PP21974P2

(12) United States Plant Patent
Smits

(10) Patent No.: US PP21,974 P2
(45) Date of Patent: Jun. 14, 2011

(54) *THUJA* PLANT NAMED 'FILIPS MAGIC MOMENT'

(50) Latin Name: *Thuja occidentalis*
Varietal Denomination: Filips Magic Moment

(75) Inventor: Edwin Johannes Arnoldes Smits, Volkel (NL)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 12/660,965

(22) Filed: Mar. 8, 2010

(51) Int. Cl.
*A01H 5/00* (2006.01)

(52) U.S. Cl. ..... Plt./213

(58) Field of Classification Search ..... Plt./213
See application file for complete search history.

(56) References Cited

OTHER PUBLICATIONS

Upov Plant Variety Database 2010/05 p. 1.*

* cited by examiner

*Primary Examiner* — Annette H Para
(74) *Attorney, Agent, or Firm* — C. A. Whealy

(57) ABSTRACT

A new and distinct cultivar of *Thuja* plant named 'Filips Magic Moment', characterized by its compact, upright and conical plant habit; moderately vigorous growth habit; and golden yellow green-colored leaves.

1 Drawing Sheet

Botanical designation: *Thuja occidentalis.*
Cultivar denomination: 'FILIPS MAGIC MOMENT'.

BACKGROUND OF THE INVENTION

The present invention relates to a new and distinct cultivar of *Thuja* plant, botanically known as *Thuja occidentalis*, and hereinafter referred to by the name 'Filips Magic Moment'.

The new *Thuja* plant is a naturally-occurring branch mutation of *Thuja occidentalis* 'Smaragd', not patented. The new *Thuja* plant was discovered by the Inventor on a single plant within a population of plants of the parent selection during the summer of 2000 in a controlled outdoor nursery environment in Volkel, The Netherlands.

Asexual reproduction of the new *Thuja* plant by cuttings in a controlled environment in Volkel, The Netherlands since October, 2000, has shown that the unique features of this new *Thuja* plant are stable and reproduced true to type in successive generations.

SUMMARY OF THE INVENTION

Plants of the new *Thuja* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Filips Magic Moment'. These characteristics in combination distinguish 'Filips Magic Moment' as a new and distinct cultivar of *Thuja:*

1. Compact, upright and conical plant habit.
2. Moderately vigorous growth habit.
3. Golden yellow green-colored leaves.

Plants of the new *Thuja* can be compared to plants of the parent, 'Smaragd'. Plants of the new *Thuja* differ from plants of 'Smaragd' in the following characteristics:

1. Plants of the new *Thuja* grow slower than plants of 'Smaragd'.

2. Plants of the new *Thuja* and 'Smaragd' differ in leaf coloration as plants of 'Smaragd' have green-colored leaves.

Plants of the new *Thuja* can be compared to plants of *Thuja occidentalis* 'Yellow Ribbon', not patented. Plants of the new *Thuja* differ from plants of 'Yellow Ribbon' in the following characteristics:

1. Plants of the new *Thuja* are more compact than and not as open as plants of 'Yellow Ribbon'.
2. Plants of the new *Thuja* are not as vigorous as plants of 'Yellow Ribbon'.

BRIEF DESCRIPTION OF THE PHOTOGRAPH

The accompanying colored photograph illustrates the overall appearance of the new *Thuja* plant, showing the colors as true as it is reasonably possible to obtain in colored reproductions of this type. Colors in the photograph may differ slightly from the color values cited in the detailed botanical description which accurately describe the colors of the new *Thuja* plant. The photograph comprises a side perspective view of a typical plant of 'Filips Magic Moment' grown in an outdoor nursery.

DETAILED BOTANICAL DESCRIPTION

The aforementioned photograph and following observations, measurements and values describe plants grown in an outdoor nursery in Volkel, The Netherlands during the autumn and under conditions which closely approximate commercial *Thuja occidentalis* production. During the production of the plants day temperatures ranged from 8° C. to 20° C. and night temperatures ranged from 1° C. to 12° C. Plants were three years old when the photograph and description were taken. In the following detailed description, color references are made to The Royal Horticultural Society Colour Chart, 2007 Edition, except where general terms of ordinary dictionary significance are used.

Botanical classification: *Thuja occidentalis* 'Filips Magic Moment'.

Parentage: Naturally-occurring branch mutation of *Thuja occidentalis* 'Smaragd', not patented.

Propagation:

*Type.*—By cuttings.

*Rooting time.*—About five months.

*Root description.*—Fine, fibrous; brown and white in color.

*Rooting habit.*—Freely branching; dense.

Plant description:

*Plant and growth habit.*—Perennial coniferous shrub; compact, upright and conical plant habit; moderately vigorous growth habit.

*Plant height.*—About 36.5 cm.

*Plant diameter.*—About 24.2 cm.

*Branching habit.*—Freely branching with about 26 lateral branches; plants maintain their lower branches and foliage to the soil level.

*Lateral branch description.*—Length: About 15.8 cm. Diameter: About 3.5 mm. Internode length: About 7.5 mm. Strength: Strong. Texture: Smooth. Color: Developing branches: Close to between 143B and 144A. One-year old branches: Close to 166C. Oldest branches: Close to 200A to 200B.

*Leaf description.*—Appearance/arrangement: Flattened and appressed, scale-like; opposite, simple; sessile. Quantity per lateral branch: About 2,450. Length: About 2.5 mm. Width: About 1.5 mm. Shape: Ovate. Apex: Broadly apiculate. Base: Cuneate. Margin: Entire. Venation pattern: Veins are not visible. Fragrance: Cedar-like. Texture: Smooth, glabrous. Color: Developing leaves, upper and lower surfaces: Close to 163B; with development, close to 153C to 153D tinged with close to 11A. Fully expanded leaves, upper and lower surfaces: Close to 137C to 143B.

Cone description: Cone development has not been observed on plants of the new *Thuja*.

Temperature tolerance: Plants of the new *Thuja* have been observed to tolerate temperatures from about −20° C. to about 35° C.

Pathogen/pest resistance: Plants of the new *Thuja* have not been observed to be resistant to pests and pathogens common to *Thuja* plants.

It is claimed:

1. A new and distinct *Thuja* plant named 'Filips Magic Moment' as illustrated and described.

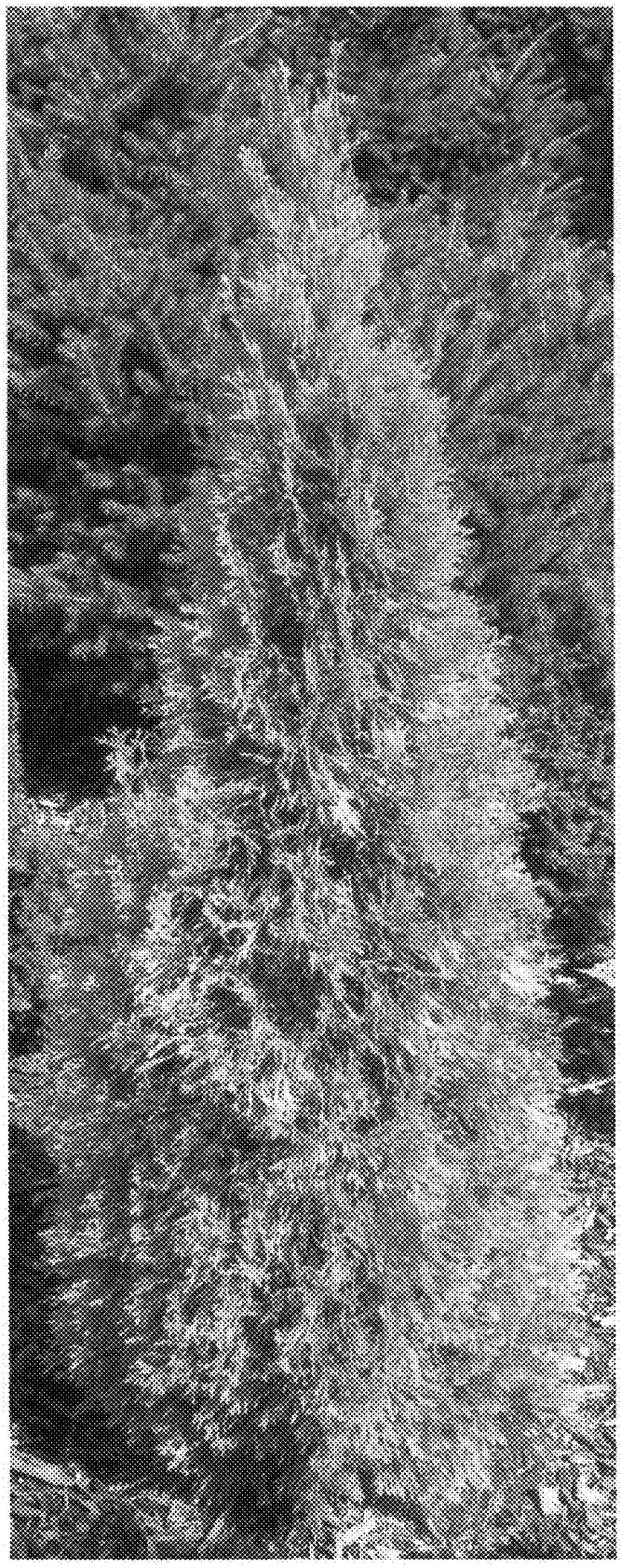

* * * * *